(12) United States Patent
Lin et al.

(10) Patent No.: US 6,496,560 B1
(45) Date of Patent: Dec. 17, 2002

(54) MOTION CORRECTION FOR PERFUSION MEASUREMENTS

(75) Inventors: Zhongmin Steve Lin, Solon, OH (US); Shalabh Chandra, Twinsburg, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 09/990,544

(22) Filed: Nov. 21, 2001

(51) Int. Cl.$^7$ .............................. G01N 23/04; A61B 6/03
(52) U.S. Cl. ............................................... 378/62; 378/8
(58) Field of Search ........................... 378/4, 8, 19, 62, 378/901

(56) References Cited

U.S. PATENT DOCUMENTS 5,602,891 A * 2/1997 Pearlman ................ 250/363.01

OTHER PUBLICATIONS

Miles, et al. "Functional Computed Tomography", 1997.
Koenig, et al. "Perfusion CT of the Brain: Diagnostic Approach for Early Detection of Ischemic Stroke", Radiology 1998; 209:85–93.
Roberts, et al., "Dynamic CT Perfusion to Assess the Effect of Carotid Revascularization in Chronic Cerebral Ischemia", AJNR 21:421–425, Feb. 2000.
Press, et al. "Numerical Recipes in C", Second Edition, pp. 412–420.
Maes, et al. "Multimodality Image Registration by Maximization of Mutual Information", IEEE Trans. Med. Imag. Vo. 16, No. 2, 1997, pp. 187–198.
Holden, et al. "Voxel Similarity Measures for 3–D Serial MR Brain Image Registration", IEEE Trans. Med. Imag. Vo. 19, No. 2, 2000, pp. 94–102.
Studholme, et al. "Automated Three–Dimensional Registration of Magnetic Resonance and Positron Emission Tomography Brain Images by Multiresolution Optimization of Voxel Similarity Measures", Med. Phys. 24(1) 1997, pp 25–35.

* cited by examiner

*Primary Examiner*—David V. Bruce
(74) *Attorney, Agent, or Firm*—Fay, Sharpe, Fagan, Minnich & McKee, LLP

(57) ABSTRACT

A CT scanner (10) for obtaining a medical diagnostic image of a subject includes a stationary gantry (12), and a rotating gantry (14) rotatably supported on the stationary gantry (12) for rotation about the subject. A plurality of temporally displaced volume images are gathered, divided into slices, and stored in slice memories ($54_1$, $54_2$, . . . $54_n$). A slice comparitor (58) compares each slice to a selected reference slice. The slices are transformed by a slice transformer (60) to align the slices thereby correcting for movement of the subject over the scan period.

21 Claims, 3 Drawing Sheets

MOTION CORRECTION FOR PERFUSION MEASUREMENTS

BACKGROUND OF THE INVENTION

The present invention relates to the art of medical diagnostic imaging. It finds particular application in conjunction with calculating tissue perfusion using computed tomography (CT) scanners, and will be described with particular reference thereto. However, it is to be appreciated that the present invention is also amenable to other modalities such as MRI, and is not limited to the aforementioned application.

Generally, CT scanners have a defined examination region or scan circle in which a patient, or subject being imaged is disposed on a patient couch. A fan beam of radiation is transmitted across the examination region from an radiation source, such as an x-ray tube, to an oppositely disposed array of radiation detectors. The x-ray tube and associated power supply and cooling components are rotated around the examination region while data is collected from the radiation detectors. Rotation of the radiation source is often achieved by mounting the radiation source to a rotating gantry which is rotated on a stationary gantry. For volume imaging, the patient couch is moved longitudinally. Continuous movement achieves spiral scanning whereas discrete steps achieve a series of parallel slices.

The sampled data is typically manipulated via appropriate reconstruction processors to generate an image representation of the subject which is displayed in a human-viewable form. Various hardware geometries have been utilized in this process. In third generation scanners, both the source and detectors rotate around the subject. In a fourth generation scanner, the x-ray source rotates and the detectors remain stationary. The detector array typically extends 360° around the subject in a ring outside of the trajectory of the x-ray tube.

In a perfusion study, blood flow in tissues and vessels of interest is of primary concern. Typically, a contrast agent is injected into the subject and multiple "snapshots" of the region of interest are taken over time. Present CT scanners are capable of taking 1 to 2 snapshots per second of the region, providing a series of images that tracks the contrast agent in near-real time.

One particular application of CT perfusion is helping to diagnose cerebral ischemia in patients who have suffered acute strokes. This type of study requires precise measurements over a period of time. One technique that is used in the calculation of perfusion is the maximum slope method, which calculates the maximum slope of a time vs. density curve and a maximum arterial enhancement. Perfusion is the maximum slope divided by the maximum arterial enhancement. Accuracy of the quantitative data is impacted by noise in the data, which may have several possible sources. These include patient motion, blood recirculation, partial volume effect, and other factors.

One method of reducing patient motion in a head CT scan, and thus improving the quality of the perfusion investigation, is immobilizing the head of the subject in an external restraint. Typically, such a device includes a strap that is connected to the patient couch that traverses the forehead of the subject, effectively eliminating head motion in a vertical direction (given that the subject is laying horizontally). However, the subject is still capable of movement laterally, as well as slight rotation of the head. These movements can seriously degrade the quality of a perfusion study, causing misalignment of the series of images, blurring a resultant image, and having adverse effects on the calculation of blood perfusion. The maximum density enhancement, measured in Hounsfield units (HU) can be reduced by 40% or more by motion that can occur despite the aid of a head restraint. The blurred images, and effects on perfusion measurements significantly impact the accuracy of quantitative measurements used in diagnosis.

Further, background noise is a factor that affects perfusion calculation, as well as the images associated therewith. Regions that exhibit low signal can be overshadowed by noise. In low blood flow regions, the maximum density enhancement and the noise can both be in the 2–4 Hounsfield unit range. Legitimate perfusion signals can be hidden decreasing the efficacy of the study as a whole. Filters meant to eliminate noise may also eliminate low strength perfusion signals effectively getting rid of good information along with useless information.

The present invention contemplates a new and improved method and apparatus which overcome the above-referenced problems and others.

SUMMARY OF THE INVENTION

In accordance with one aspect of the present invention, a method of compensating for subject motion is provided. A plurality of volume images is gathered and a central slice image is selected. Movement in two dimensions is determined for each central slice image relative to a reference central slice image. The images are corrected in accordance with the determined movement.

In accordance with another aspect of the present invention, a diagnostic imaging device is provided. An imaging region receives a portion of a subject. A reconstruction processor reconstructs a plurality of volume images. A slice comparitor compares the images and a slice transformer adjusts the images in accordance with the comparison.

In accordance with another aspect of the present invention, a computed tomography device is provided. A source of penetrating radiation emits radiation into an imaging region. A detection means detects the radiation after it has passed through a subject. A reconstruction means reconstructs volume images of the subject. A means for tracking tracks movement of the images over time, a means for determining determines a movement correction for the images, and a means for applying applies the movement correction to the images.

One advantage of the present invention is a reduction of the negative effects of patient motion.

Another advantage resides in a reduction of the partial volume effect.

Another advantage resides in the reduction of the negative effects of blood recirculation.

Another advantage resides in the reduction of the effect of low amplitude signals.

Another advantage resides in the increased accuracy of curve fits.

Another advantage resides in reduction of errors caused by noise.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps

DETAILED DESCRIPTION OF THE PREFERRED EMBODIMENTS

Figure 1:
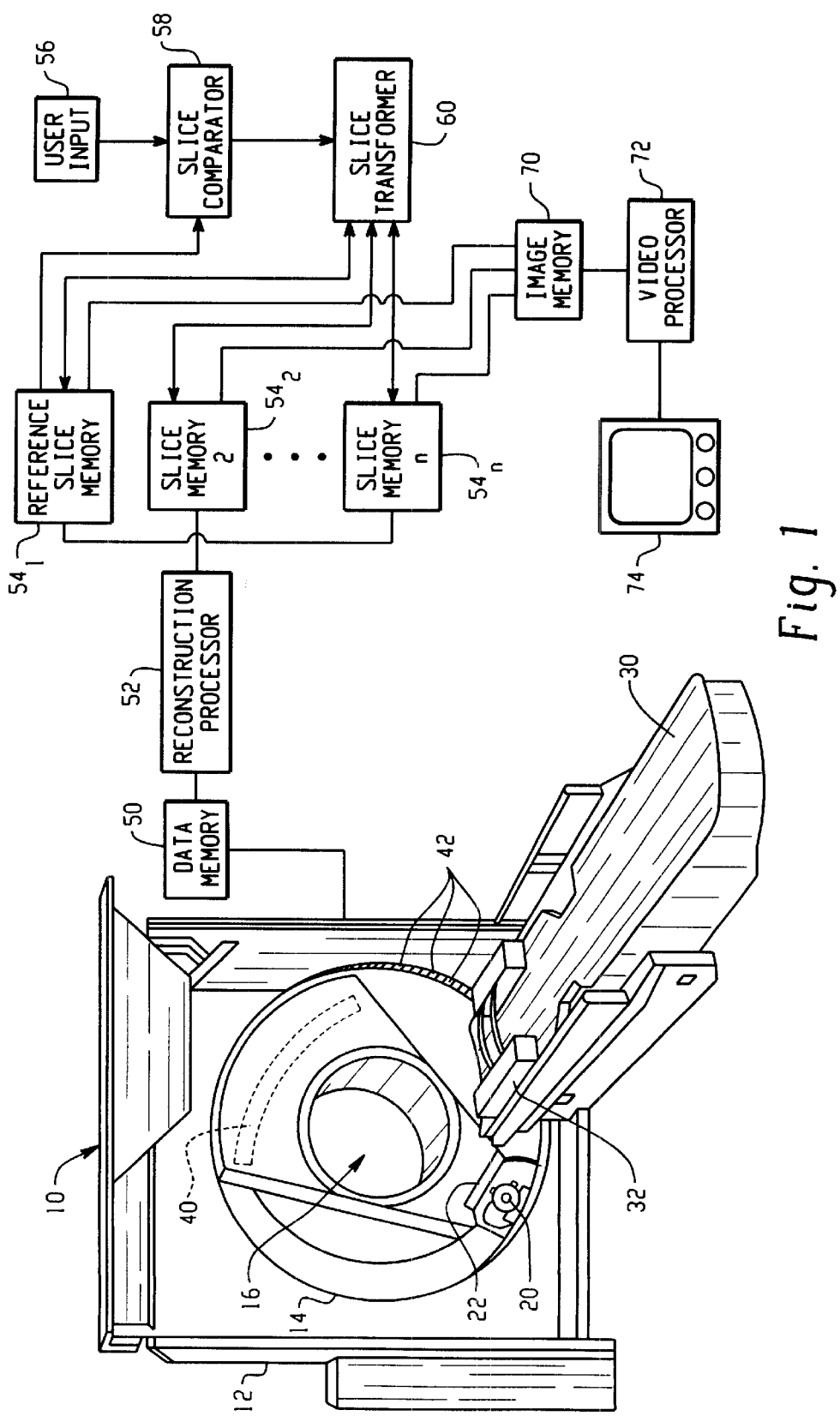
FIG. 1 is a diagrammatic illustration of a computed tomography scanner in accordance with the present invention.

With reference to FIG. 1, a CT scanner 10 includes a stationary gantry 12 and a rotating gantry 14 which define an imaging region 16. The rotating gantry 14 is suspended from the stationary gantry 12 for rotation about the examination region 16. A radiation source 20, such as an x-ray tube, is arranged on the rotating gantry 14 for rotation therewith. The radiation source 20 produces a beam of penetrating radiation that passes through the examination region 16 as the rotating gantry 14 is rotated by an external motor (not illustrated) about a longitudinal axis of the examination region 16. A collimator and shutter assembly 22 forms the beam of penetrating radiation into a cone shape and selectively gates the beam on and off. Alternately, the radiation beam is gated on and off electronically at the source 20. A subject support 30, such as a radiolucent couch or the like, suspends or otherwise holds a subject being examined or imaged at least partially within the examination region 16 such that the cone-shaped beam of radiation defines a volume through the region of interest of the subject. A radiolucent head restraint 32 restricts the mobility of the subject's head.

The imaged volume is repeatedly imaged over a period of time. In a perfusion study, a contrast agent is injected into the subject and factors relating to blood flow of the subject are monitored over a period of time to track blood flow behavior in the region of interest. The volume is segmented into a three dimensional array of voxels, which are often conceptualized as a series of slices, each slice having a finite thickness.

In a third generation CT scanner, an array of radiation detectors 40 is mounted peripherally across from the source on the rotating gantry. In a fourth generation CT scanner, a stationary ring of radiation detectors 42 is mounted around the stationary gantry 12. Regardless of the configuration, the radiation detectors are arranged to receive the radiation emitted from the source 20 after it has traversed the imaging region 16.

The radiation detectors 40, 42 convert the detected radiation into electronic projection data. That is, each of the radiation detectors produces an output signal which is proportional to an intensity of received radiation. Each radiation detector generates data elements which correspond to projections along a corresponding ray within the view. Each element of data in a projection or data line is related to a line integral of an attenuation coefficient taken along its corresponding ray passing through the subject being reconstructed.

A data memory or buffer 50 receives the sampled data from the radiation detectors. The data memory 50 optionally performs filtering or other operations before passing the data to a reconstruction processor 52 which reconstructs volume image representations of the subject.

In the preferred embodiment, the gantry 14 makes approximately 40 turns around the subject, to produce 40 volume images of the region of interest which are stored in a first series of image memories. Of course, the number of images can be more or less, 40 is a balance between factors such as time of scan, radiation dose to the subject, cardiac cycle, and a period of time wherein useful perfusion information can be gathered. Typical present day CT scanners can generate 40 images in about 20–40 seconds, which is a relatively long time that the subject is asked to remain perfectly motionless. In order to correct for inevitable patient motion, a registration processor analyzes the volume images and aligns them such that the region of interest remains stationary over the course of the images.

The registration processor selects a corresponding reference slice in each of the 40 volume images which it stores in a reference slice memory $54_1$, and actively calculates a movement function. The reference slice is preferably a central slice. In the preferred embodiment, a diagnostician is presented (on a user input terminal 56) with an image of the reference slice. This first image of the reference slice is used as the norm to which each subsequent or preceding time-step image is compared and adjusted to match. Each other image is stored in a corresponding memory $54_2, \ldots 54_n$.

Figure 2:
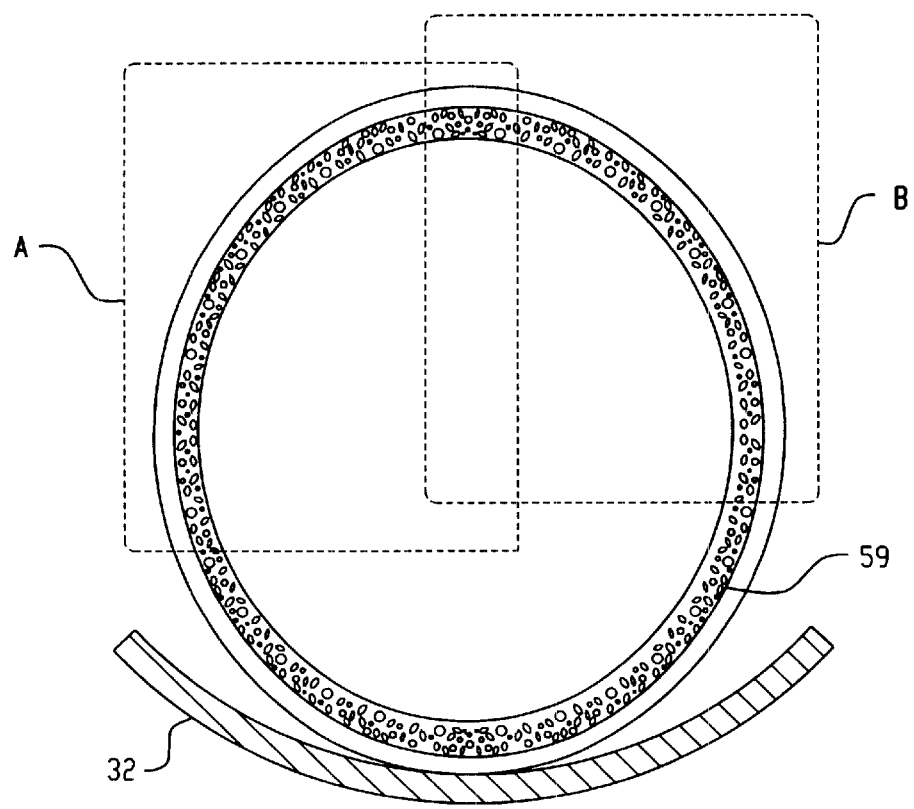
FIG. 2 is an illustration of an axial slice of the skull of the subject including exemplary user selected subregions.
Figure 3:
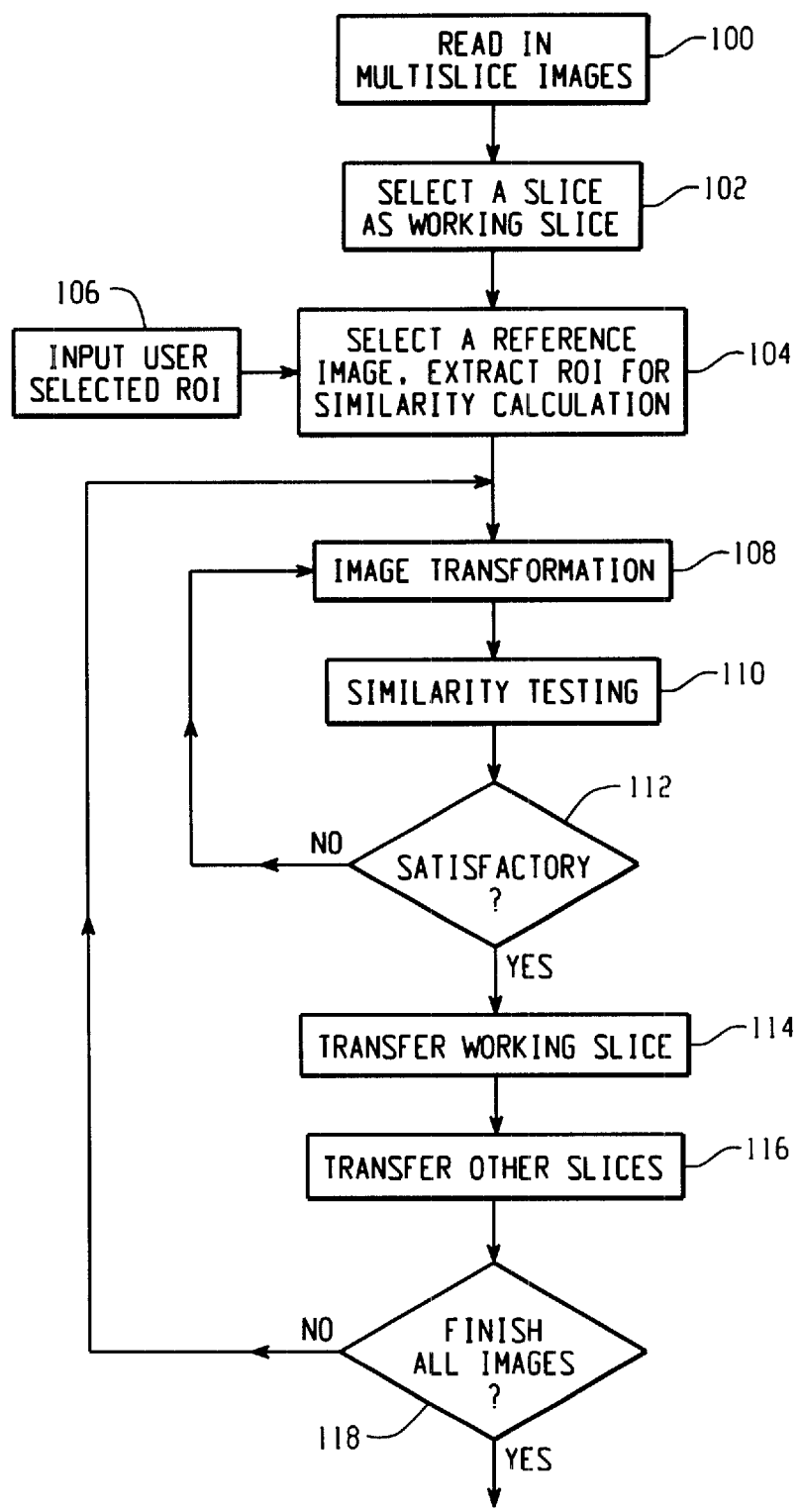
FIG. 3 is a flow diagram that includes integral steps of the present invention.

Preferably, the registration processor includes a comparitor 58 that identifies landmarks which are easy to identify, shapely defined and appear in diverse parts of the slice. In a brain perfusion scan, an exemplary landmark is a portion of the skull, having constant shape and intensity from image to image over the whole scan period. Optionally, the diagnostician can crop the slice to a subregion of interest to reduce processing time. With reference to FIG. 2, Exemplary subregions A and B are indicated. The subregions include at least a portion of the top and a side of the skull 59 of the subject. Selecting these portions of the skull makes minute motions of the subject more detectable. One of A and B can be used as the subregion of the reference slice.

Each subsequent image of the reference slice is searched in this manner for the selected region, and each subsequent image is shifted or rotated to bring the landmarks into alignment with the reference image by a slice transformer 60. As the registration processor 56 aligns these images, it records a movement function for each of the 40 volume images that describes its movement relative to the reference slice. Especially in a head scan, the region of interest can be considered a rigid body, and any movement that the reference slice undergoes, the entire imaging volume undergoes. The recorded movement function is applied to each slice of the corresponding volume image to align the remainder of the imaging volume. Alternately, and more time intensive, the alignment process can be performed individually for each slice of each volume. Other alignment processes and algorithms are also contemplated.

Some voxels within the region of interest have weak time-density curves. More specifically, some voxels have amplitudes that are comparable with noise. The preferred embodiment groups similar weak signals and combines them to make characteristic stronger signals.

After the reconstruction processor 52 has reconstructed the volume images of the region of interest, the volume images are divided into slices and stored in a high resolution slice image memory. The slice image memory includes n submemories, where n is the number of slices in the imaging volume. That is, the first slice of the 40 temporally displaced volume images from the beginning of the scan to the end of the scan are stored in order in a first slice submemory, the images of the second slice are stored in a second slice submemory, and so on to the images of the nth slice which are stored in an nth submemory. In the preferred embodiment, the slices are each one voxel thick. In the preferred embodiment, a 512×512 image matrix is used, and each slice is one voxel thick. That is, the 40 density values from each corresponding voxel in the 40 slices define a time vs. density curve. Therefore, in the preferred embodiment in which each slice is 512×512, there are 512×512 time density curves per slice.

The intensity values of the corresponding voxels of the 40 volume images define a time density curve. Each time density curve is a measure of the amount of contrast agent within the subregion corresponding to the same voxel in each of the time displaced volume images. A typical time-density curve includes a leading edge during which the contrast agent is entering the voxel region rapidly, a maximum at which time the contrast agent is at a maximum concentration, and a trailing edge during which the contrast agent is leaving the voxel. The curve typically is a gamma-variate curve which is characterized by its steep leading edge and gradual trailing edge.

A maximum enhancement processor searches for the maximum enhancement value of the time-density curves of the voxels within an artery region indicated by the diagnostician on the reference slice. More specifically, the maximum intensity processor searches for the maximum enhancement among all voxels in a diagnostician indicated artery region. The maximum enhancement of the artery is used later in a perfusion calculation.

The high resolution slices are passed through a filter and subsequently reduced in resolution by a resolution reducer. The resolution reducer takes a high resolution image matrix of each slice in time, groups the voxels, and combines each group of voxels, e.g. averages, maximum intensity, etc. In the preferred embodiment, the high resolution matrices are 512×512, and the low resolution matrices are 128×128. The resolution reducer bins the voxels into groups of 16 by position, that is, 4×4 groups of high resolution voxels are combined into a single low resolution voxel. After the volume images over the whole scan time are reduced in resolution, they are stored in a low resolution memory.

The low resolution images are used to calculate a number of factors that are later used in the perfusion calculation. More specifically, a low signal filter eliminates low signals. The low signal filter identifies the voxels that have time-density curves too weak or too poorly defined to be used by themselves. At least one of multiple criteria is used to determine which signals are too weak. One method is to compare the time-density curve to a curve model. Voxels having curves outside of a preselected range of fit to the model are discarded as having low signal. Another method is to find a peak enhancement value of the time density curve for each voxel. Voxels with peak enhancements lower than a preselected threshold enhancement value are discarded as having low signal. Another method of identifying low signal voxels is selecting voxels that are historically of low signal, e.g. bone.

Typically, the patient's circulatory system recirculates the contrast agent back through the region of interest causing a secondary intensity peak. If the secondary peak is included in the gamma-variate curve fitting, the peak is shifted later in time altering the slope of the leading edge. A clipping circuit clips the secondary peak based on percentage intensity drop from the maximum, a time after the maximum, or a combination of the two. A processor replaces the clipped region with a gamma variate curve segment or other extrapolation of the remaining curve portion. A curve fitting processor compares the time-density curves to a model curve. Data that is not within a preselected tolerance of the ideal curve is filtered out as bad data.

More specifically, a gamma-variate curve smoothing circuit smooths the time density curve of each voxel to reduce noise. The smoothed curves are mathematically fit to a gamma-variate curve. More specifically, the value K, value $\alpha$, and value $\beta$ that define a gamma variate curve mathematically are calculated. Voxels that have a better fit to the gamma-variate model typically have a stronger signal, and are thus more robust for use in the perfusion calculation. A maximum slope calculator calculates the maximum slope of the region of the time-density curve from the K, $\alpha$, and $\beta$ values.

A blood perfusion value is now calculated for each voxel. In a preferred embodiment a perfusion calculator divides the maximum slope value for each voxel by the maximum artery enhancement found the maximum enhancement processor to obtain a perfusion value for each voxel. An interpolator interpolates the truncated time-density curve to form representative curves. Alternately, the K, $\alpha$, $\beta$, and maximum enhancement values can address a preloaded look-up table to retrieve the perfusion value. These values are stored in a perfusion image memory 70 A video processor 72 places data from the perfusion image memory 70 in proper format for a video monitor 74.

Voxels identified as having low amplitude time density curves are identified and sorted by a processor. optionally, the low amplitude data is temporally filtered to eliminate curves that are not generally contemporaneous to the curves of neighboring voxels. A sorter sorts the time-density curves into groups. Each group is averaged, or summed, or otherwise combined by a curve averaging processor and the combined time density curve replaces the time density curve of all curves in the group. The sorter, in the preferred embodiment, groups the voxels using one of k-means clustering, c-means clustering, and fuzzy logic. It is to be understood that other methods of grouping voxels may also be utilized. The curve averaging processor groups voxels with similar characteristics together. The voxels are determined to be similar based on at least one of its x-coordinate position, its y-coordinate position, its peak enhancement value, a time the time density curve takes to reach the peak enhancement value (time-to-peak), the Hounsfield number, and the like. Once the time density curves are grouped and combined, the groups are passed to the curve fitting processor. This greatly reduces the inherent noise in the signals as the noise tends to cancel out as the signals are averaged. Thus, the averaged signal has a higher signal-to-noise ratio than the individual curves of any of the constituent voxels of the group. The curve fitting processor fits the combined time-density curve and fits it to the model curve. A common perfusion value is determined for all the constituent voxels of the group.

For example, the voxels are grouped by x and y-coordinate positions. This scheme yields voxel groups containing constituent voxels that are physically close to each other. In another example, voxels are grouped solely by maximum Hounsfield number, voxels with maximum Hounsfield values of 2–4 HU are grouped together, and voxels with values of 4–8 HU are grouped together, regardless of spatial position. Preferably, the combination of criteria that best serves each individual perfusion study is selected. In this manner, one perfusion image is made from the normal signal voxels and the plurality of low-signal voxel groups.

With reference to FIG. 2, the major steps of a preferred embodiment are presented in flowchart form. In a reading step, 100, multislice images are read into the device. In a selection step 102 a working slice is selected. In a reference selection step 104 user input 106 is used to select a reference image and select a region of interest therein. In a transformation step 108, the image is transformed. In a testing step 110 the image is compared for similarity with the reference image, and deemed satisfactory or unsatisfactory in step 112. Satisfactory slices are transferred in steps 114 and 116. The process is repeated 118 until all of the slices have been aligned.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of compensating for motion of a subject undergoing a tissue perfusion analysis including:
   gathering a plurality of volume images of a region of interest over a period of time;
   selecting a corresponding central slice image in each volume image;
   determining movement in two dimensions for each central slice image relative to a reference central slice image;
   correcting the volume images in accordance with the determined movement.

2. The method as set forth in claim 1, wherein the movement determining step further includes:
   generating a movement function that describes movement of the central slice image over the plurality of volume images;
   and the correcting step includes:
   correcting for movement in each volume image by applying the movement function of the corresponding slice images of the volume image.

3. The method as set forth in claim 2, wherein the central slice images of the volume images are aligned, then other slice images of the volume images are aligned utilizing the movement function as a map of alignment.

4. The method as set forth in claim 1, further including after selecting a central slice image:
   selecting a subregion of the selected central slice image and wherein the movement determining step is performed on the subregion of the corresponding slice images.

5. The method as set forth in claim 4, wherein the step of selecting a subregion includes:
   selecting at least a portion of a top of a skull of the subject; and,
   selecting at least a portion of a side of the skull of the subject.

6. The method as set forth in claim 1, wherein the step of selecting the subregion includes a user designating the subregion on a display of the selected central slice image.

7. The method as set forth in claim 1, further including:
   transforming other slice images in each volume image with a two dimensional linear interpolation to align the other slices with the central slice.

8. The method as set forth in claim 7, the step of selecting a subregion includes:
   comparing a transformed other slice image to the central slice image of the same volume image and computing a similarity measure, the similarity measure providing a quantitative measure of difference in positions of the compared slice images.

9. The method as set forth in claim 8, further including:
   shifting the transformed other image if the similarity measure is outside of a preselected tolerance.

10. The method as set forth in claim 8, wherein the similarity measure yields a measure of the similarity between a field of view of the central slice image to a field of view of the other slice image.

11. The method as set forth in claim 1, further including:
    limiting motion of the region of interest of the subject to motion in two dimensions with an external subject restraint device.

12. A diagnostic imaging device for performing tissue perfusion investigations that compensates for subject motion, the device including:
    an imaging region for receiving a region of interest of a subject;
    a reconstruction processor for converting data gathered by the device into a series of volume image representations of the region of interest;
    a slice comparitor that compares at least portions of reference in each of the volume images with each other and relative movement of the reference slices;
    a transformer that aligns the reference slices with each other.

13. The diagnostic imaging apparatus as set forth in claim 12, wherein the slice transformer adjusts a first slice so coordinates of a subregion in the first slice match coordinates of a corresponding subregion in a second slice.

14. The diagnostic imaging device as set forth in claim 13, wherein the image transformer adjusts subsequent, slices so coordinates of the subregion in each of the slices match the coordinates of the subregion in the first slice.

15. The diagnostic imaging device as set forth in claim 12, further including:
    a function generator that generates a movement function in time that describes the relative movement of the reference slices.

16. The diagnostic imaging apparatus as set forth in claim 15, wherein the movement function is applied to the volume images to align the volume images with each other.

17. The diagnostic imaging device as set forth in claim 12, further including:
    an external restraint for restraining a region of interest of the subject against movement within the imaging region, limiting possible motion of the region of interest to two dimensions.

18. A computed tomography device for performing perfusion studies comprising:
    a source of penetrating radiation that produces radiation for transmission into an imaging region of the device;
    a detection means that detects the radiation after it traverses the imaging region;
    a reconstruction means that reconstructs the detected radiation into temporally displaced volume images of a region of interest of a subject in the imaging region;
    a means for tracking movement of a corresponding volume image subregion across the plurality of volume images;
    a means for determining a movement correction for each of the plurality of subregions;
    a means for applying the movement corrections to the volume images.

19. The computed tomography device as set forth in claim 18, wherein the subregion is a single imaging slice.

20. The computed tomography device as set forth in claim 18, wherein the subregion is a user-selected portion of a slice.

21. The computed tomography device as set forth in claim 18, wherein the subregion is a two dimensional subsection.

* * * * *